United States Patent
Hess et al.

(10) Patent No.: US 10,752,958 B2
(45) Date of Patent: Aug. 25, 2020

(54) IDENTIFICATION OF MICROORGANISMS FROM GENOME SEQUENCING DATA

(71) Applicant: Santa Clara University, Santa Clara, CA (US)

(72) Inventors: David Hess, San Jose, CA (US); Farid Tadros, San Jose, CA (US); Michael Jared Lumpe, San Jose, CA (US); Eileen Wagner, Berkeley, CA (US); Mark W. Pandori, San Francisco, CA (US)

(73) Assignee: Santa Clara University, Santa Clara, CA (US)

( * ) Notice: Subject to any disclaimer, the term of this patent is extended or adjusted under 35 U.S.C. 154(b) by 777 days.

(21) Appl. No.: 15/592,483

(22) Filed: May 11, 2017

(65) Prior Publication Data

US 2017/0327904 A1  Nov. 16, 2017

Related U.S. Application Data

(60) Provisional application No. 62/334,831, filed on May 11, 2016.

(51) Int. Cl.

| | | |
|---|---|---|
| *C12Q 1/6888* | (2018.01) | |
| *G16B 20/00* | (2019.01) | |
| *G16B 25/00* | (2019.01) | |
| *G16B 50/00* | (2019.01) | |
| *G16B 30/00* | (2019.01) | |
| *G16H 50/20* | (2018.01) | |
| *C12Q 1/689* | (2018.01) | |

(52) U.S. Cl.
CPC ........... *C12Q 1/6888* (2013.01); *G16B 20/00* (2019.02); *G16B 25/00* (2019.02); *G16B 30/00* (2019.02); *G16B 50/00* (2019.02); *C12Q 1/689* (2013.01); *G16H 50/20* (2018.01); *Y02A 90/26* (2018.01)

(58) Field of Classification Search
None
See application file for complete search history.

(56) References Cited

PUBLICATIONS

Shendure et al. Next-generation DNA sequencing Nature Biotechnology vol. 26, pp. 1135-1145 (Year: 2008).*
Rosen et al. Metagenome Fragment Classification Using N-Mer Frequency Profiles Advances in Bioinformatics vol. 2008, article ID 205969 (Year: 2008).*
Taylor et al. Fungal multilocus sequence typing-it's not just for bacteria Current Opinion in Microbiology vol. 6 pp. 351-356 (Year: 2003).*
Didelot et al. Transforming clinical microbiology with bacterial genome sequencing Nature Reviews Genetics vol. 13, pp. 601-612 (Year: 2012).*

\* cited by examiner

*Primary Examiner* — John S Brusca
(74) *Attorney, Agent, or Firm* — Lumen Patent Firm

(57) ABSTRACT

A diagnostic analysis method and system is provided for identifying a microorganism from a genome sequence. Partially or fully assembled microbial genomes or short reads from whole-genome sequencing of microbial genomes are processed into a 4 MB Boolean array while preserving 1% of the genomic information in a way that allows for rapid comparison of a query genome to a large reference database. This represents a critical savings in storage space and speed by which large reference libraries can be queried.

3 Claims, 7 Drawing Sheets

NSA (210) for example: ATGAC

FIG. 4

FNLS (220) neighbors of NSA

NSM | ... NSA FNLS .... NSA FNLS ...... NSA FNLS ...

FIG. 5

Reference Array with *mx1* Elements Ordered Alphabetically

```
Element 1 = 11 A bases
Element 2 = 10 A bases, 1 C base
.
.
.
.
Element m = 11 T bases
```

FIG. 6

Boolean Array with 1 by *m* elements for FLNS (230)

```
Element 1              = 0
Element 2              = 1
Element 3              = 0
Element 4              = 1
Element 5              = 1
  •
  •
Element 1,000,000      = 0
Element 1,000,001      = 1
  •
  •
Element m              = 0
```

FIG. 7

Boolean Array with *mxn* elements for microorganisms (310)

```
                        Organism 1
                        Organism 2
                                   ...  Organism n Element 1            =  0  0       ..   0
Element 2            =  1  0       ..   1
Element 3            =  0  1       ..   1
Element 4            =  1  1       ..   0
Element 5            =  1  0       ..   1
    .
    .
Element 1,000,000    =  0  1       ..   1
Element 1,000,001    =  1  0       ..   1
    .
    .
Element m            =  0  1       ..   0
```

FIG. 8

Diagnostic Score (120)

Let $\|v\|_1$ be the number of ones in vector v.

input is a (1 x $m$) boolean vector.

Reference is a ($m$ x $n$) matrix with boolean vectors of reference organisms in rows.

intersections = input * Reference is a (1 x $n$) vector of intersection counts between the input and all reference sequences.

scores is a (1 x $n$) vector of similarity scores in the range [0, 1], such that:

$$\text{scores}_i = \frac{\text{intersections}_i}{\|\text{input}\|_1 + \|\text{Reference}_i\|_1 - \text{intersections}_i}$$

FIG. 9

IDENTIFICATION OF MICROORGANISMS FROM GENOME SEQUENCING DATA

This application claims priority from U.S. Provisional Patent Application 62/334,831 filed May 11, 2016, which is incorporated herein by reference.

FIELD OF THE INVENTION

This invention relates to methods and systems for identification of microorganisms from whole genome sequencing data.

BACKGROUND OF THE INVENTION

Whole genome sequencing has opened several avenues of new research and has expanded our biological knowledge. Tens of thousands of microbial isolates have been whole genome sequenced representing over 1,500 different species. Thousands of new genomes are added each year to public databases. To harness the diagnostic potential of this genomic information it is critical that the genome information be compressed into the same format regardless of the method used to generate the sequence. Furthermore, this format must enable comparisons of a new clinical sample to the database of tens of thousands of genomes and be scalable as we add more genomes to public databases. These comparisons must be performed accurately and in a timely manner to be useful for clinical diagnostics. The lack of such a solution has been noted to be the primary reason whole genome sequencing is not being widely adopted for diagnostic purposes. The present invention advances the art and provides technology for better clinical diagnosis.

SUMMARY OF THE INVENTION

A diagnostic analysis method and system is provided for identifying a microorganism from a genome sequence. A nucleotide sequence (NSM) is generated from a sample of a microorganism by sequencing the sample of the microorganism using a genome sequencing device. The generated nucleotide sequence of the organism (NSM) is then scanned for each incidence of presence of a nucleotide sequence anchor (NSA). The nucleotide sequence anchor (NSA) has a fixed nucleotide length of 4, 5 or 6 nucleotides. In a preferred embodiment, the nucleotide sequence anchor (NSA) has a fixed nucleotide length of 5 nucleotides.

At each incidence of presence of the nucleotide sequence anchor (NSA), a finite length nucleotide sequence (FLNS) neighboring each of the nucleotide sequence anchors (NSAs) is identified. The finite length nucleotide sequence (FLNS) has a fixed nucleotide length of 9, 10, 11, 12 or 13 nucleotides. In a preferred embodiment, the finite length nucleotide sequence (FLNS) has a fixed nucleotide length of 11 nucleotides.

For each of the identified finite length nucleotide sequences (FLNSs), the identified finite length nucleotide sequences (FLNSs) are scored with reference to an alphabetized nucleotide reference array. Each element in the alphabetized nucleotide reference array has the same nucleotide length as defined for the finite length nucleotide sequence (FLNS). The scoring of the FLNSs results in an FLNS Boolean array with each element in the array representing the presence or absence of the finite length nucleotide sequence (FLNS) relative to the position in the reference array.

Transforming the FLNS Boolean array with a reference Boolean database matrix generates a diagnostic score. The reference Boolean database matrix is a stored database and contains data for one or more reference organisms, which has been generated according to the same steps to obtain a Boolean representation as outlined above. A species represented by the sample of the microorganism is identified from the diagnostic score.

Examples of the invention can be embodied as a method, device or system employing structures or devices to deploy executable method steps. Such structures involve a computer processor capable of executing programmable code for the processes, a computer storage medium for storing information generated by or needed for the processes, and a computer output medium to output the diagnostic score and identified species to a user in a meaningful visual representation.

Embodiments of the invention have the following results or advantages:

1. Conversion from a genome sequence to the particular file format as taught herein is fast. We have converted ~50,000 microbial genomes into this format in under 2 hours. A single new genome can be converted and compared to the database of ~50,000 genomes in a few seconds.
2. The final file sizes are small (less than 4 MB per genome) and useable in any analysis that works on Boolean arrays giving the file format additional flexibility.
3. The additional flexibility enables development that needs rigorous vetting and analysis before product launch because calculations can be performed extremely fast when using Boolean arrays.
4. Embodiments of the invention produce very low incidence of false positives, while still retaining high sensitivity (absence of false negatives).

BRIEF DESCRIPTION OF THE DRAWINGS

FIG. 4 shows a 5-letter nucleotide sequence anchor (NSA) according to an exemplary embodiment of the invention.

FIG. 5 shows a nucleotide sequence of a microorganism (NSM) scanned for nucleotide sequence anchor (NSA) and finding neighboring finite length nucleotide sequence(s) (FLNS) according to an exemplary embodiment of the invention.

FIG. 6 shows a reference array of according to an exemplary embodiment of the invention.

FIG. 7 shows according to an exemplary embodiment of the invention a boolean array for FLNS identified with respect to the reference array shown in FIG. 6. "0" means FLNS not identified in reference array, and "1" means FLNS identified in reference array.

FIG. 8 shows according to an exemplary embodiment of the invention a boolean array for n microorganisms with identifiers whether the their scanned/identified FLNS are present with respect to the reference array shown in FIG. 6. "0" means FLNS not identified in reference array, and "1" means FLNS identified in reference array.

FIG. 9 shows intersection counts obtained by matrix multiplication (matrix of FIG. 7 matrix of FIG. 8) and a diagnostic score according to an exemplary embodiment of the invention.

DETAILED DESCRIPTION

Figure 1:
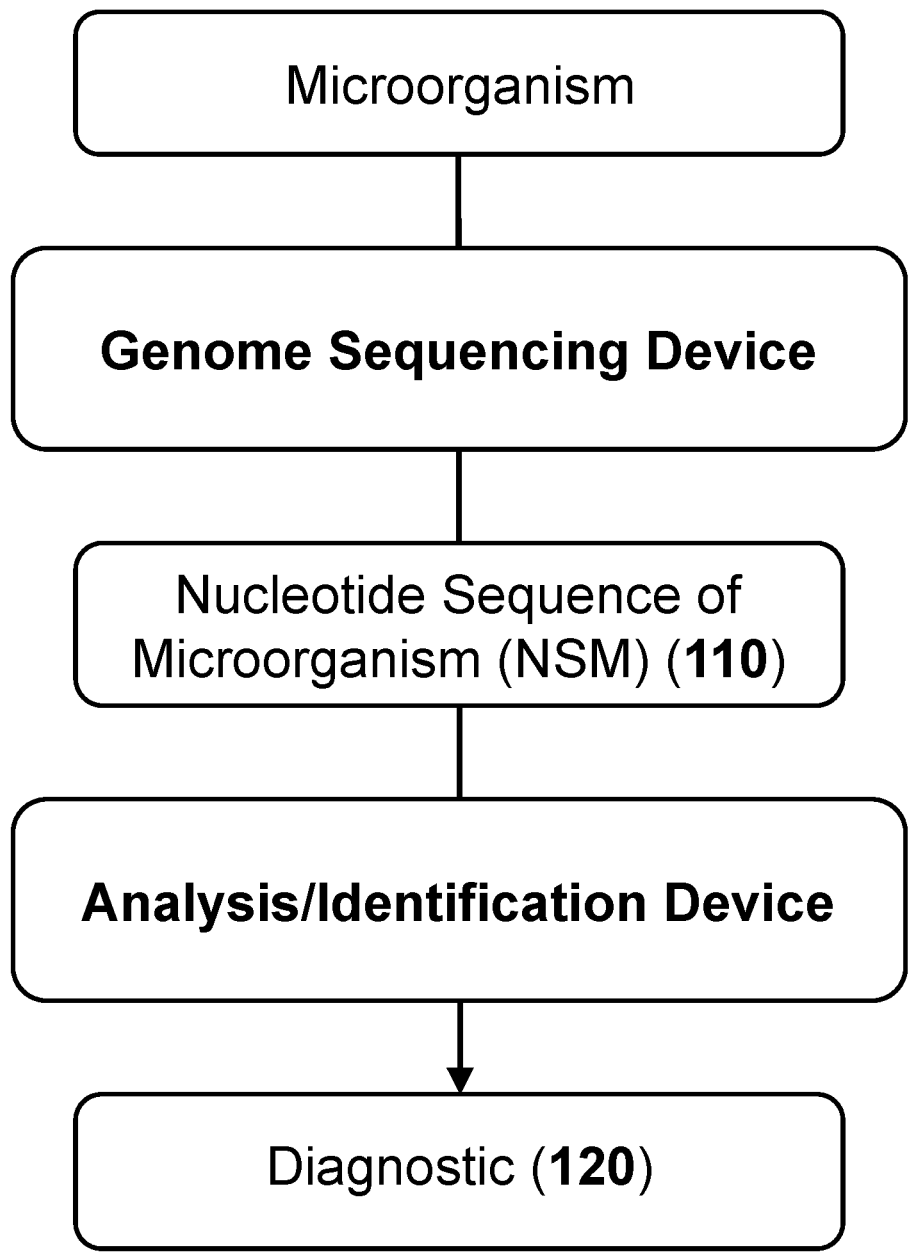
FIG. 1 shows an overview of the diagnostic analysis of microorganisms according to an exemplary embodiment of the invention.
Figure 2:
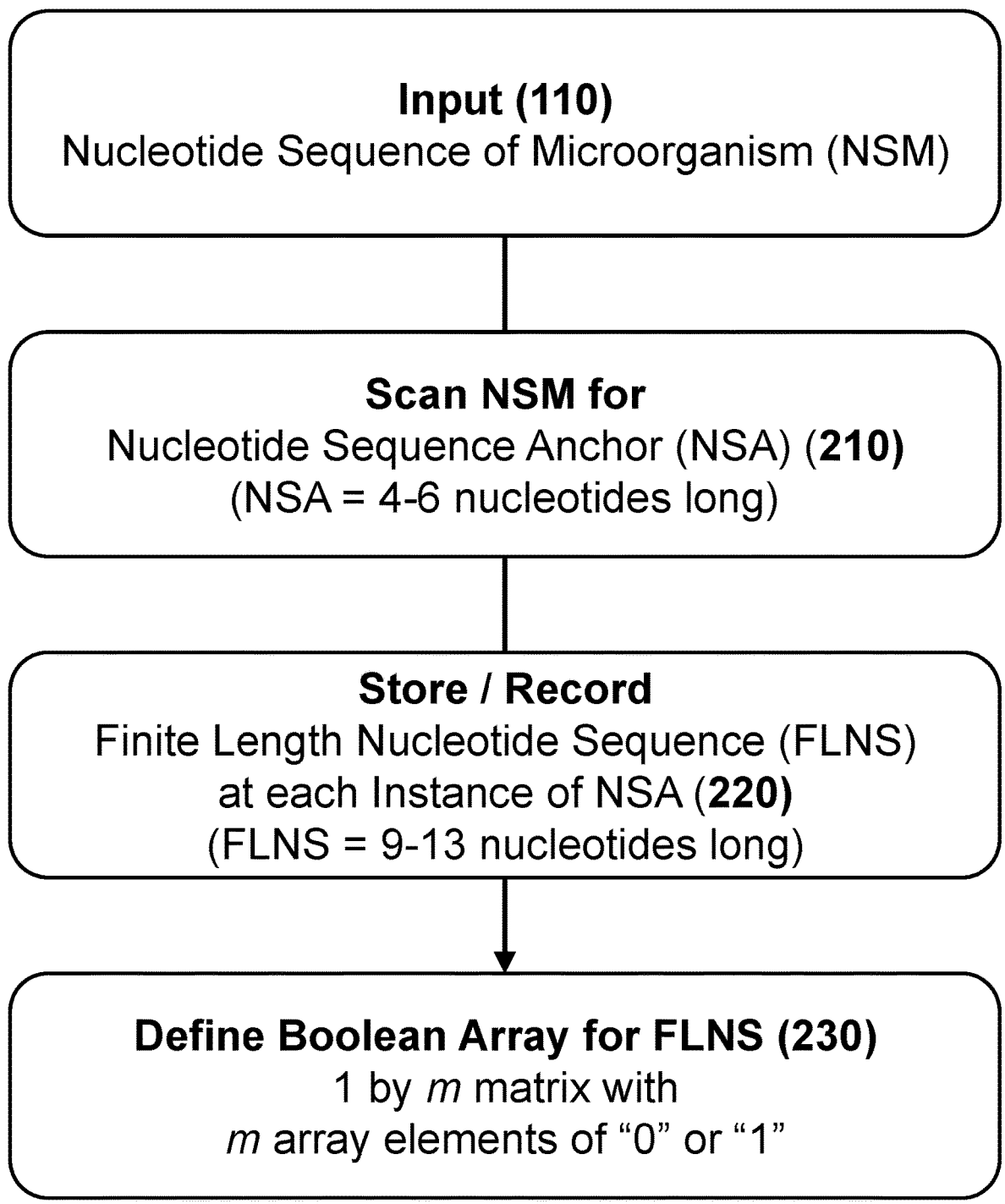
FIGS. 2-3 show the analysis and identification process according to an exemplary embodiment of the invention.
Figure 3:
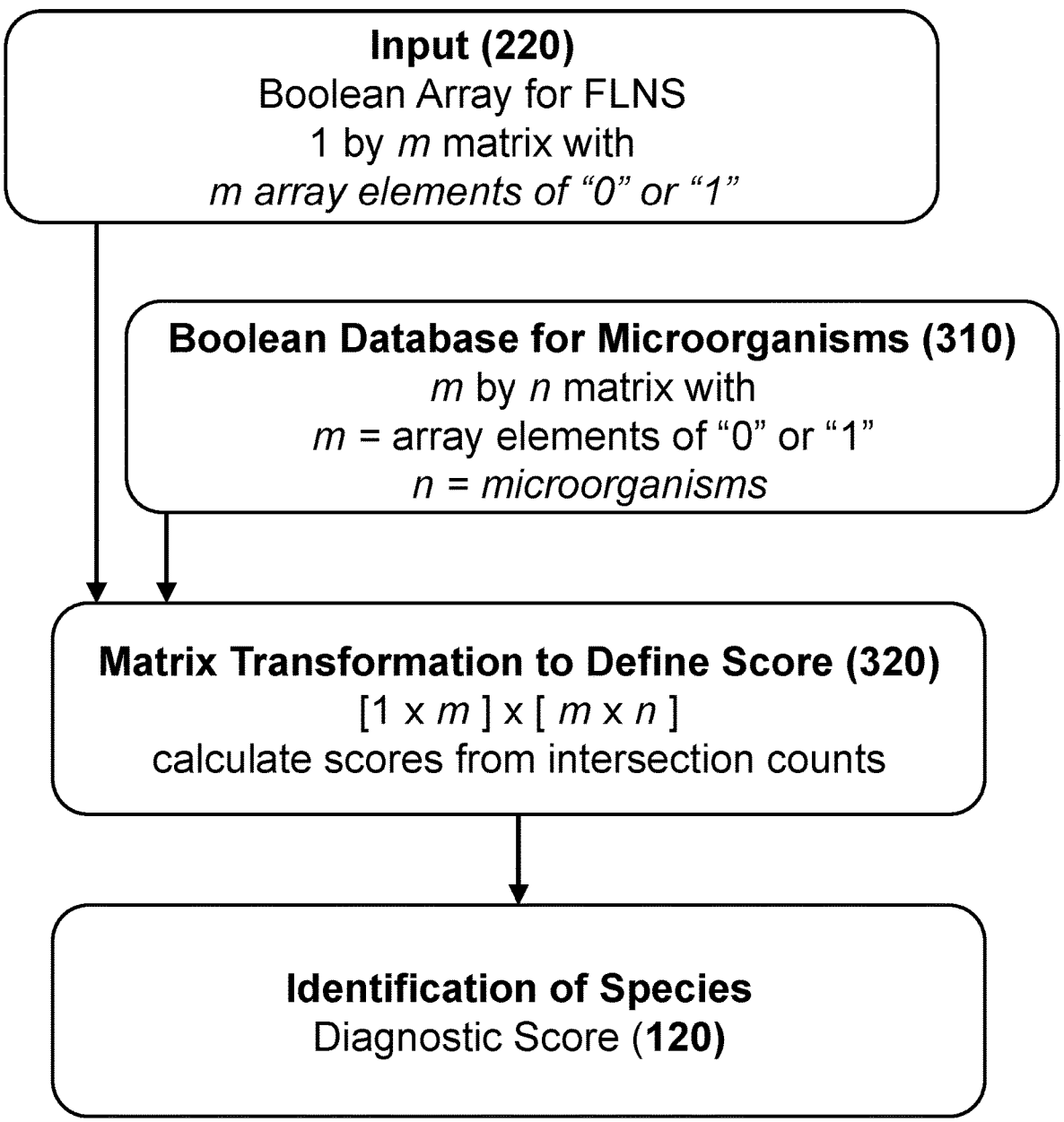

The method of this invention computer processes partially or fully assembled microbial genomes (.fasta file format) or short reads from whole-genome sequencing of microbial genomes (.fastq file format) into a 4 MB Boolean array while preserving 1% of the genomic information in a way that allows for rapid comparison of a query genome to a large reference database. This represents a critical savings in storage space (.fastq files are 300 GB while .fasta files for assembled genomes are 300 MB) and speed by which large reference libraries can be queried. This is accomplished by scanning the .fasta or .fastq file for each instance of the nucleotide sequence 'ATGAC'. This 5 letter 'anchor' (NSA) will occur at random about 1 in 1000 times in a microbial genome. The software then stores the next 11 nucleotides (FLNS) temporarily. When a typical microbial genome is searched this way, there are usually between 4,000 and 11,000 unique 11 nucleotide sequences stored, representing between 1-2% of the total genomic information. These sequences are alphabetized then converted into the 4 MB Boolean array. Since DNA has a 4 letter alphabet, there are only 4,194,304 (4^11) unique sequences that are 11 nucleotides long. The array is designed such that element 1 represents that sequence of 11 A bases with a 1 meaning the sequence is found in the genome and a 0 meaning the sequence is not found in that particular genome. The array elements progress through all 4,194,304 unique sequences in alphabetical order. This way rather than storing the sequences themselves which would be very memory intensive or create larger file sizes that were difficult to compare—our system just stores 4,194,304 '1's or '0's in a compact file format. Furthermore, because these arrays are very sparse (only about 0.25% of elements are ones) they can be efficiently compressed, reducing storage requirements from 4 MB per genome to less than 4.5 KB.

The additional innovation of using these Boolean arrays is the speed and ease by which a single query genome can be compared against a large database of reference genomes. Currently, the National Institutes of Health has a curated database (RefSeq) with over 70,000 microbial genomes. These reference genomes could be converted into our Boolean array system in a matrix that is only ~280 GB. This matrix may be efficiently compressed into a sparse representation that requires only ~300 MB of storage, and a database of one million reference sequences stored in this way would require only 4.5 GB. The query genome having been converted into our Boolean array format can be multiplied through matrix multiplication into the reference matrix. The resulting transformed matrix will only have a '1' where the query genome and the reference genome exactly share an 11 nucleotide sequence following the anchor 'ATGAC'. Using a Jaccard Scoring method (which is the fraction of elements in either array which are common to both)—we quickly generate a biologically useful comparison score between the query genome and every reference genome in the database. The highest score from among all the reference genomes in the database provides the Genus and species identification of the query genome and if the score passes certain thresholds—it also provides important subspecies identification (i.e. *Salmonella enterica* serotype). The ability to convert large whole genome sequencing files to 4 MB Boolean arrays allows for rapid genome comparisons against large databases in a manner that does not currently exist in the published literature.

We implemented a full reference database based on RefSeq downloaded on 03-03-2016 which contained whole genome files for 61,242 microorganisms. We received 64 .fastq files from the Alameda Public Health Laboratories generated from microorganisms received by their lab for testing with traditional species identification. While performing traditional species identification, they also performed DNA extraction, followed by whole genome sequencing on an Illumina MiSeq to produce the .fastq files. Based on the traditional species identifications we have a gold standard to test our method against.

We ran our query software on a Mac OS X machine with 12 3.46 GHz Intel core processors and 128 GB 1333 MHz DDR ECC Ram. Rapid assemblies were via TADPOLE de novo genome assembler were performed on the .fastq files which took ~90 seconds per genome. This assembly removes the vast majority of sequencing noise and checks to make sure the sequence is of sufficient quality to procedure (2 .fastq files were rejected at this step). The remaining 62 partially assembled genomes (.fasta file format) were converted to our Boolean vector array format and queried against the database of Boolean vector arrays representing all 61,242 microorganisms in RefSeq. We generated three comparison scores for each of the 62 queries files based on different scoring methods: Jaccard, Hamming Distance and Asymmetric Jaccard. Each file was queried and scored in ~5 seconds per file. The total processing time per file was ~95 seconds. It currently takes 60 hours for the Alameda Public Health Laboratories to generate the .fastq files, so our total analysis time about three orders of magnitude faster than that step in the process. This compares to 4-5 days using traditional identification methods performed by Alameda County Public Health Labs. Half of these tests result in inconclusive identification and are sent to the California State Public Health Labs for further testing with identifications being reported 2-4 weeks later. Our workflow is substantially faster and requires much less man-hours as well as being more accurate.

Analysis of each of the three scoring methods (standard Jaccard, asymmetric Jaccard, and Hamming Distance) showed that the standard Jaccard performed best. The following results use the standard Jaccard score, which ranges between 0 and 1 with higher values representing closer matches. A genus or species prediction is only made when the score exceeds a predefined significance threshold, otherwise the result is marked "no prediction." Thresholds are set conservatively in order to minimize the rate of false positives. 59 of the 62 queries generated Jaccard scores of 0.5 or higher and all 59 matched the genus and species provided by the Alameda Public Health Laboratories traditional methods. The three samples with Jaccard scores less than 0.5 matched reference species that were sparsely represented in the RefSeq (two had a single representative of that species and the other had two representatives of that species. For comparison, *E. coli* has 4,519 representative genomes and *K. pneumoniae* has 996 representatives). Of these final three samples, 2 correctly identified the genus and species, while the lowest scoring sample only correctly identified the genus. While we are still refining significance thresholds for our scores, we believe these bottom three would be well below the threshold for reporting both genus and species. It remains to be seen if any of them would meet the threshold for reporting genus. Overall, the initial implementation of our query method with a database built from all microbial genomes in RefSeq was extremely successful. It also demonstrates the importance of scalability—the ease of adding additional members of sparsely covered species such as *Plesiomonas shigelloides, Enterobacter cloacae* and *Pro-*

*teus vulgaris*. As sequence databases grow, our reference database will keep pace and improve the output scores.

It should be noted that the method according to the invention results into a so-called "embarrassingly parallel" problem, in that it can be split up into many tasks that require no communication between them. A query can be trivially parallelized across as many CPU cores or separate machines as needed by dividing the rows of the reference genome array between them, allowing the database to scale to a virtually unlimited number of reference organisms. Because the core of our method is a matrix multiplication, it can make use of one of the many available software libraries and frameworks for performing parallel or distributed linear algebra calculations.

Examples

Legend for Examples (the Three Example Below this Legend Refer to the Numerals of the Legend)
1. query_file: input partially assembled whole genome sequence
2. top_score: highest jaccard score match in the reference database (scores are between 0-1)
3. predicted_genus: predicted genus of the sequenced sample based on comparison, this field is blank if top_score is not greater than genus_threshold
4. predicted_species: predicted species of the sequenced sample based on comparison, this field is blank if top_score is not greater than species_threshold
5. top_genus: genus of best genome match to the query genome
6. genus_threshold: if top_score is greater than this number then a predicted_genus is reported
7. top_species: species of best genome match to the query genome
8. species_threshold: if top_score is greater than this number then a predicted_species is reported
9. top_strain: strain identified from the NCBI database of the top match based on Jaccard score
10. top_description: metadata descriptors associated with the top_strain from the NCBI database
11. top_accession: NCBI database accession number for the top_strain Example 1
1. 4_S3_L001_R_001.FASTA
2. 0.979105651
3. *SALMONELLA*
4. *ENTERICA*
5. *SALMONELLA*
6. 0.2
7. *ENTERICA*
8. 0.58255285
9. CVM N38848
10. [GCF_001479785.1] *SALMONELLA ENTERICA* SUBSP. *ENTERICA SEROVAR INFANTIS* (ENTEROBACTERIA)
11. GCF 001479785.1

Example 2

1. 032416-3_S3_L001_R_001.FASTA
2. 0.792345226
3. *ESCHERICHIA*
4. *COLI*
5. *ESCHERICHIA*
6. 0.2
7. *COLI*
8. 0.6537444
9. GN02055
10. [GCF_001519445.1] *ESCHERICHIA COLI* (*E. COLI*)
11. GCF_001519445.1

Example 3

1. 12388_S19.FASTA
2. 0.895443618
3. *KLEBSIELLA*
4. *PNEUMONIAE*
5. *KLEBSIELLA*
6. 0.2
7. *PNEUMONIAE*
8. 0.707796395
9. CHS112
10. [GCF_001031325.1] *KLEBSIELLA PNEUMONIAE* (ENTEROBACTERIA)
11. GCF_001031325.1

What is claimed is:

1. A diagnostic analysis method for identifying a microorganism from a genome sequence, comprising:
  (a) producing a nucleotide sequence (NSM) from a sample of a microorganism by sequencing the sample of the microorganism using a genome sequencing device;
  (b) scanning the nucleotide sequence of the organism (NSM) for each incidence of presence of a nucleotide sequence anchor (NSA), wherein the nucleotide sequence anchor (NSA) has a fixed nucleotide length of 4, 5 or 6 nucleotides;
  (c) at each incidence of presence of the nucleotide sequence anchor (NSA), identifying a finite length nucleotide sequence (FLNS) neighboring each of the nucleotide sequence anchors (NSAs), wherein the finite length nucleotide sequence (FLNS) has a fixed nucleotide length of 9, 10, 11, 12 or 13 nucleotides;
  (d) for each of the identified finite length nucleotide sequences (FLNSs), scoring the identified finite length nucleotide sequences (FLNSs) with reference to an alphabetized nucleotide reference array, wherein each element in the alphabetized nucleotide reference array has the same nucleotide length as defined for the finite length nucleotide sequence (FLNS), wherein the scoring results in an FLNS Boolean array with each element in the array representing the presence or absence of the finite length nucleotide sequence (FLNS) relative to the position in the reference array;
  (e) providing a stored reference Boolean database matrix for one or more reference organisms which has been generated according to the steps 1(a-d);
  (f) generating a diagnostic score by transforming the FLNS Boolean array with the reference Boolean database matrix;
  (g) identifying a species represented by the sample of the microorganism from the diagnostic score,
  wherein the steps 1(b)-(g) are performed using a computer processor capable of executing programmable code for the steps 1(b)-(g), a computer storage medium for storing information generated by or needed for the steps 1(b)-(g), and a computer output medium to output the diagnostic score and identified species to a user in a meaningful visual representation.

2. The method as set forth in claim 1, wherein the nucleotide sequence anchor (NSA) has a fixed nucleotide length of 5 nucleotides.

3. The method as set forth in claim 1, wherein the finite length nucleotide sequence (FLNS) has a fixed nucleotide length of 11 nucleotides.

* * * * *